(12) United States Patent
Han et al.

(10) Patent No.: US 10,835,408 B2
(45) Date of Patent: Nov. 17, 2020

(54) POWERED METHOD FOR AUGMENTING A JOINT FUNCTION OF A HUMAN

(71) Applicant: Otto Bock HealthCare LP, Austin, TX (US)

(72) Inventors: Zhixiu Han, Acton, MA (US); Christopher Williams, Pittsburgh, PA (US); Jeff Anthony Weber, San Francisco, CA (US); Christopher Eric Barnhart, Carlisle, MA (US); Hugh M. Herr, Somerville, MA (US); Richard James Casler, Jr., Lowell, MA (US)

(73) Assignee: Otto Bock HealthCare LP, Austin, TX (US)

( * ) Notice: Subject to any disclaimer, the term of this patent is extended or adjusted under 35 U.S.C. 154(b) by 457 days.

(21) Appl. No.: 15/653,986

(22) Filed: Jul. 19, 2017

(65) Prior Publication Data
US 2017/0319369 A1    Nov. 9, 2017

Related U.S. Application Data

(62) Division of application No. 13/347,443, filed on Jan. 10, 2012, now Pat. No. 9,839,552.

(60) Provisional application No. 61/431,277, filed on Jan. 10, 2011.

(51) Int. Cl.
*A61H 3/00* (2006.01)
*A61F 5/01* (2006.01)

(52) U.S. Cl.
CPC ........... *A61F 5/0127* (2013.01); *A61H 3/008* (2013.01); *A61H 2201/123* (2013.01); *A61H 2201/1215* (2013.01); *A61H 2201/149* (2013.01); *A61H 2201/165* (2013.01); *A61H 2201/1647* (2013.01); *A61H 2201/5038* (2013.01); *A61H 2201/5069* (2013.01); *A61H 2201/5084* (2013.01); *A61H 2201/5097* (2013.01); *A61H 2205/106* (2013.01); *A61H 2205/12* (2013.01)

(58) Field of Classification Search
CPC . A61F 5/0127; A61H 3/008; A61H 2201/123; A61H 2201/1215; A61H 2201/149; A61H 2201/5069; A61H 2201/5038; A61H 2201/5097; A61H 2205/106; A61H 2205/12; A61H 2201/165; A61H 2201/1647; A61H 2201/5084
See application file for complete search history.

(56) References Cited

U.S. PATENT DOCUMENTS

| | | | |
|---|---|---|---|
| 9,839,552 B2 * | 12/2017 | Han | A61H 3/008 |
| 2005/0070834 A1 * | 3/2005 | Herr | A61B 5/1038 |
| | | | 602/28 |
| 2006/0224246 A1 * | 10/2006 | Clausen | A61F 2/66 |
| | | | 623/24 |

(Continued)

*Primary Examiner* — Quang D Thanh

(57) ABSTRACT

A method for controlling a powered device to augment a joint function of a human during a gait cycle using a powered actuator that supplies an augmentation torque, an impedance, or both to a joint is disclosed. In some embodiments, the method modulates the augmentation torque, the impedance, and a joint equilibrium according to a phase of the gait cycle to provide at least a biomimetic response. Accordingly, the actuator is capable of normalizing or augmenting human biomechanical function, responsive to a wearer's activity, regardless of speed and terrain.

17 Claims, 13 Drawing Sheets

(56) References Cited

U.S. PATENT DOCUMENTS

2007/0016329 A1* 1/2007 Herr .................... A61F 2/68
                                              700/250
2009/0171469 A1* 7/2009 Thorsteinsson ...... A61B 5/1038
                                              623/26

* cited by examiner

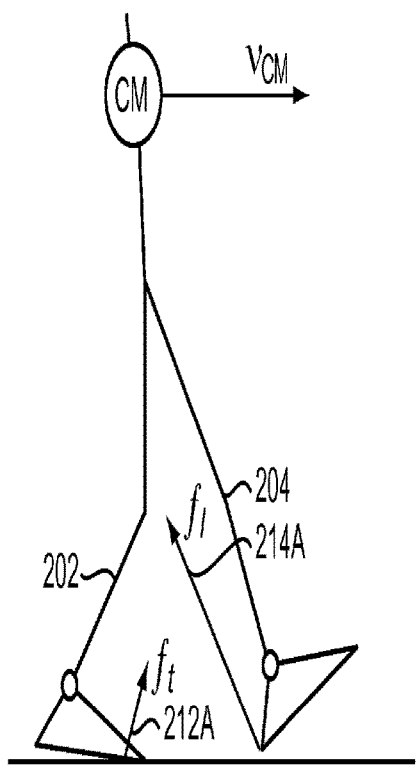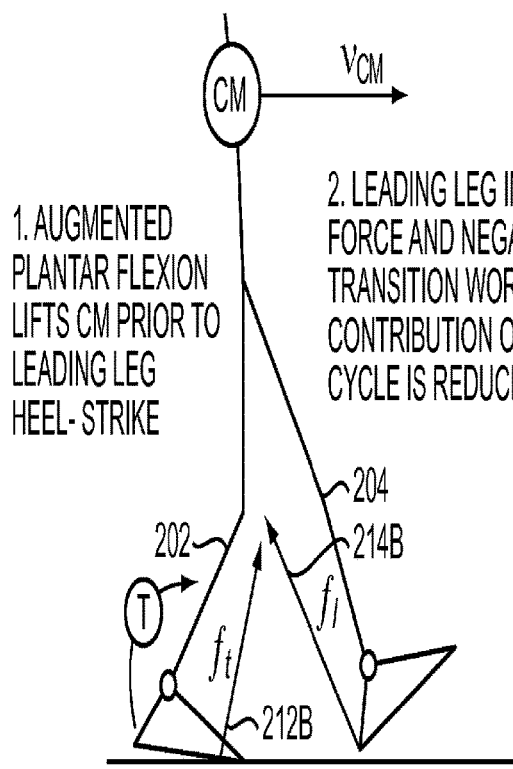
A) WEAK PLANTAR FLEXOR CASE
FIG. 2A
B) AUGMENTED PLANTAR FLEXOR
FIG. 2B

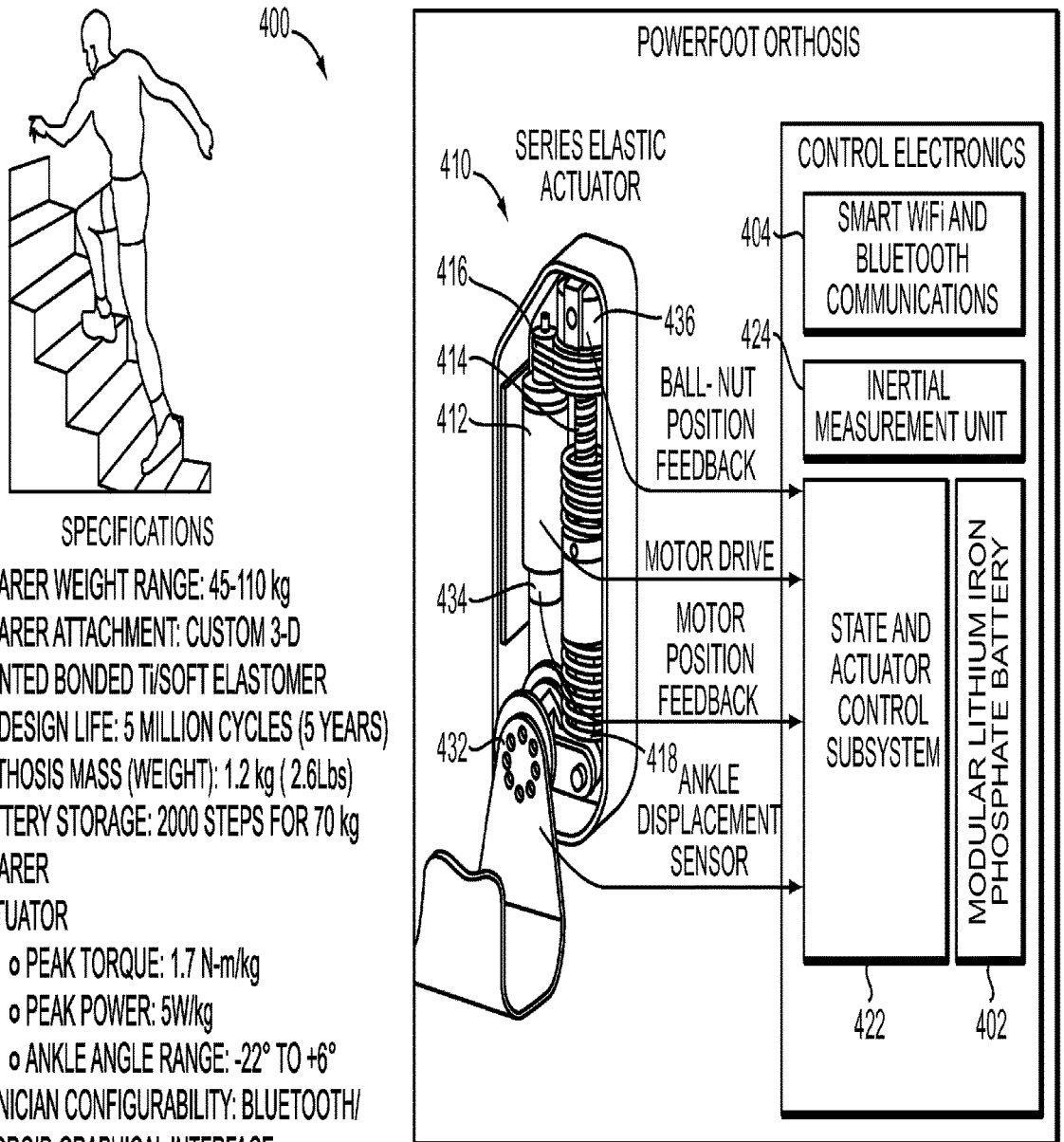

SPECIFICATIONS

- WEARER WEIGHT RANGE: 45-110 kg
- WEARER ATTACHMENT: CUSTOM 3-D PRINTED BONDED Ti/SOFT ELASTOMER
- L1 DESIGN LIFE: 5 MILLION CYCLES (5 YEARS)
- ORTHOSIS MASS (WEIGHT): 1.2 kg (2.6Lbs)
- BATTERY STORAGE: 2000 STEPS FOR 70 kg WEARER
- ACTUATOR
  - PEAK TORQUE: 1.7 N-m/kg
  - PEAK POWER: 5W/kg
  - ANKLE ANGLE RANGE: -22° TO +6°
- CLINICIAN CONFIGURABILITY: BLUETOOTH/ ANDROID GRAPHICAL INTERFACE
- RESEARCH: REAL-TIME, WiFi DATA ACQUISITION: (50 STATE VARIABLES AT 500 HZ)

FIG. 4A

POWERED METHOD FOR AUGMENTING A JOINT FUNCTION OF A HUMAN

RELATED APPLICATIONS

This application is a division of U.S. patent application Ser. No. 13/347.443 filed on Jan. 10. 2012 (now U.S. Pat. No. 9,839,552), which claims priority to and benefit of U.S. Provisional Patent Application Ser. No. 61/431,277, filed on Jan. 10, 2011, the entire content of which is hereby incorporated by reference in its entirety.

FIELD OF THE INVENTION

This invention relates generally to lower-extremity orthotic apparatus designed to emulate human biomechanics and to normalize function, components thereof, and methods for controlling the same.

BACKGROUND

Approximately 65% of service members seriously injured in Iraq and Afghanistan sustain injuries to their extremities. Many of these individuals experience muscle tissue loss and/or nerve injury, resulting in the loss of limb function or substantial reduction thereof. Injuries to the lower leg can be particularly devastating due to the critical importance of the ankle in providing support for body position, and in propelling the body forward economically during common functions such as level-ground walking and the ascent and descent of stairs and slopes.

Increasingly, robotic technology is employed in the treatment of individuals suffering from physical disability, either for the advancement of therapy tools or as permanent assistive devices. An important class of robotic devices provides therapy to the arms of stroke patients. Additionally, lower-extremity robotic devices have been developed for the enhancement of locomotor function. Although decades of research has been conducted in the area of active permanent assistive devices for the treatment of lower-extremity pathology, there devices are not designed to produce a biomimetic response, generally described in terms of joint torque, joint angle, and other related parameters as observed in a human not having substantial muscle tissue injury and not using any device to assist in ambulation. Therefore, the robotic devices usually result in unnatural ambulation and may even cause significant discomfort to the wearer. As such, many commercially available ankle-foot orthoses remain passive and non-adaptive to the wearer even today.

These passive devices cannot adequately address two major complications of anterior muscle weakness, which include slapping of the foot after heel strike (foot slap) and dragging of the toe during swing (toe drag). At heel strike, the foot generally falls uncontrolled to the ground, producing a distinctive slapping noise (foot slap). During mid-swing, toe drag prevents proper limb advancement and increases the risk of tripping. A conventional approach to the treatment of anterior/posterior compartment leg weakness is a mechanical brace called an Ankle Foot Orthosis (AFO). Although AFOs may offer some biomechanical benefits, disadvantages still remain. W. E. Carlson, C. L. Vaughar, D. L. Damiano, and M. F. Abel, "Orthotic Management of Gait in Spastic Diplegia," *American Journal of Physical Medicine & Rehabilitation*, vol. 76, pp. 219-225, 1997, found that AFOs did not improve gait velocity or stride length in children with cerebral palsy. Still further, J. F. Lehmann, S. M. Condon, B. J. de Lateur, and R. Price, "Gait Abnormalities in Peroneal Nerve Paralysis and Their Corrections by Orthoses: A Biomechanical Study," *Archives of Physical Medicine and Rehabilitation*, vol. 67, pp. 380-386, 1986 June, discovered that although a constant stiffness AFO was able to provide safe toe clearance in drop-foot patients, the device did not reduce the occurrence of slap foot.

Moreover, the passive devices typically do not address a dominant complication of posterior muscle weakness i.e., the lack of late stance powered plantar flexion. Since terminal stance powered plantar flexion is paramount for limiting heel strike losses of the adjacent leg, a patient with weak posterior muscles will likely experience an increase in impact force on the leading leg at heel strike and, consequently, an increase in the metabolic rate of walking. Therefore, there is a need for improved systems and methods of permanent assistive devices for the treatment of lower-extremity pathology.

SUMMARY

In various embodiments, the present invention provides devices and methods for operating/controlling such devices so as to assist patients with anterior and/or posterior compartment leg weakness by eliminating or significantly reducing foot slap and/or foot drop. This is achieved, using a type of device called a PowerFoot Orthosis (PFO); the PFO devices are capable of position, impedance, and non-conservative torque control in both dorsiflexion and plantar flexion directions in accordance with the gait-cycle, terrain (e.g., ground slope and stairs) and walking speed. The PFOs can also augment ankle torque during stance so as to perform the net non-conservative work and to deliver the mechanical power necessary to normalize the augmented ankle mechanics. Thus, the PFO devices can provide at least a biomimetic response and optionally can be used to augment normal biomechanical response. Offering control enhancement for both stance and swing phases, the PFO can be used as a permanent assistive device where actuation, sensing, power, and computation are all packaged within a small, lightweight, autonomous, manufacturable, and high cycle-life package that can readily fit beneath a normal pant leg.

In a laboratory study, a tethered powered ankle-foot orthosis was shown to reduce both foot slap and toe drag in patients with anterior muscle weakness. The PFO can help facilitate the return to physiological function of soldiers or civilians who have experienced incapacitating injuries to their anterior and/or posterior compartment leg musculature, limiting their capacity to walk. In addition to the potential for improved walking speed and ambulation economy, decreased demand on the leading limb in walking may reduce long-term morbidity and promote rapid return to physiological function. The PFO can also assist humans having uninjured anterior and/or posterior compartment leg musculature in activities such as carrying a heavy load over a long distance to enhance their strength and endurance.

In one aspect, embodiments of the invention feature a powered device for augmenting a joint function of a human during a gait cycle. The device includes a powered actuator for supplying an augmentation torque and/or an impedance to a joint, and a controller to modulate the augmentation torque, the impedance, and a joint equilibrium according to a phase of the gait cycle to provide at least a biomimetic response. The controller may be configured to modulate, within the gait cycle, the augmentation torque, the impedance, and the joint equilibrium according to a speed of ambulation, e.g., walking speed, and/or terrain. The powered actuator may include a series-elastic actuator, and the series-elastic actuator may include a transverse-flux motor.

In some embodiments, the device may also include a first sensor to generate a first sensor signal related to terrain and/or speed of ambulation, and the controller may be adapted to kinematically reconstruct a path of the joint within the gait cycle according to the first sensor signal. The device may also include an accelerometer to determine heel strike. The kinematic reconstruction may include computing a pose and an origin of a co-ordinate frame associated with a link connected to the joint and/or another joint proximal to the joint.

In some embodiments, computing the pose includes creating a homogeneous transformation of the co-ordinate frame, and the homogeneous transformation may include a 3×1 vector defining an origin of the co-ordinate frame and a 3×3 matrix comprising unit vectors of the co-ordinate frame. At least one point within the co-ordinate frame may correspond to a link connected to the joint and/or another joint proximal to the joint. In some embodiments, the joint is an ankle joint and a point that corresponds to the link may be a distal end (e.g., the knee joint) and/or a proximal end (e.g., the ankle joint) of a tibia connected to the ankle.

In some embodiments, the controller is adapted to determine a terrain type as one of substantially level surface, sloping surface, and stairs, and the controller may also be adapted to determine an activity according to the terrain type. The activity can be one of ascending stairs, descending stairs, walking on a substantially level surface, walking on a surface sloping up, and walking on a surface sloping down. The device may include a second sensor to provide a second sensor signal related to one or more of a pitch angle, a pitch velocity, an ankle angle, and joint torque, and the controller may be adapted to determine the phase of the gait cycle based at least in part on the second sensor signal.

In some embodiments, the powered actuator includes a motor, and the device further includes a third sensor configured to provide a third sensor signal related to a velocity of the motor. The device may also include a timer to provide a timing signal to the controller, and the controller may be adapted to determine the phase of the gate cycle based at least in part on the timing signal. The joint equilibrium may vary in time during the gait cycle, and the modulation may include modeling the joint equilibrium as a second-order response to a joint-position goal to be achieved prior to a next phase of the gait cycle. The modulation may also include adjusting at least the augmentation torque such that the modeled joint equilibrium is approximately equal to a pre-determined joint equilibrium. The second-order response can be an over-damped response. In some embodiments, a biomimetic response is achieved within the gait cycle. The device may also include a parallel and/or series elastic element for applying a torque to the joint, thereby dorsiflexing the joint. The joint may be an ankle joint.

In some embodiments, the controller is adapted to modulate the augmentation torque according to a positive-force feedback. The augmentation torque may be modulated according to the positive-force feedback in combination with a natural joint torque supplied by the human, such that the combined torque approximates a normal joint torque. The positive-force feedback may be adjusted according to terrain and/or ambulation speed.

In some embodiments, the controller is adapted to modulate the augmentation torque according to scaling factor. The controller may also be adapted to attenuate the augmentation torque according to a protocol. The device may include an external signal to stimulate the actuator. The impedance may be a linear impedance or a non-linear impedance.

In another aspect, embodiments of the invention feature a powered method for augmenting a joint function of a human during a gait cycle. The method includes supplying at least one of an augmentation torque and an impedance to a joint. The method also includes modulating the augmentation torque, the impedance, and a joint equilibrium according to a phase of the gait cycle to provide at least a biomimetic response.

The impedance may include a stiffness component, a damping component, and/or an inertial component. Modulating the impedance may include determining the stiffness component and/or the damping component. In some embodiments, the impedance includes a non-linear impedance, and modulating the impedance may include determining a gain of the non-linear impedance and an exponent of the non-linear impedance.

The phase of the gait cycle may be determined, at least in part, according to a sign of joint angular velocity, joint angular velocity, joint inertial rate, joint acceleration, and/or joint torque. The augmentation torque may be supplied in addition to natural joint torque supplied by the human to achieve a pre-determined total joint torque response. In some embodiments, modulating includes or consists essentially of applying a closed-loop torque control at the joint. The method may also include modeling the joint torque, and determining the phase of the gait cycle based on the joint torque model.

In some embodiments, the method further includes kinematically reconstructing a path of a proximal link connected to the joint and/or another joint proximal to the joint within the gait cycle. The kinematic reconstruction may include determining a terrain type as one of a substantially level surface, a sloping surface, and stairs. The kinematic reconstruction may also include determining an activity according to the terrain type. The activity can be one of ascending stairs, descending stairs, walking on substantially level surface, walking on a surface sloping up, and walking on a surface sloping down.

In some embodiments, the impedance is supplied to the joint during a controlled plantar flexion phase of the gait cycle in order to mitigate foot slap. The augmentation torque, the impedance, and the joint equilibrium may be modulated in order to mitigate foot drop and/or to provide a pre-determined net work according to ambulation speed, terrain, or both.

In some embodiments, the augmentation torque is modulated according to a positive-force feedback. The augmentation torque may be modulated according to the positive-force feedback in combination with a natural joint torque supplied by the human such that the combined torque approximates at least a normal joint torque. The positive-force feedback may include a gain and an exponent, and the gain and/or the exponent may be determined according to a speed of ambulation, terrain or both.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations. As used herein, the term "substantially" means ±10% and, in some embodiments, ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 2a schematically illustrates human ankle behavior in a weak plantar flexor case;

FIG. 2b schematically illustrates human ankle behavior in an augmented plantar flexor case, according to one embodiment;

FIGS. 4a and 4b illustrate two PFO devices according to two different embodiments;

DESCRIPTION

Figure 1:
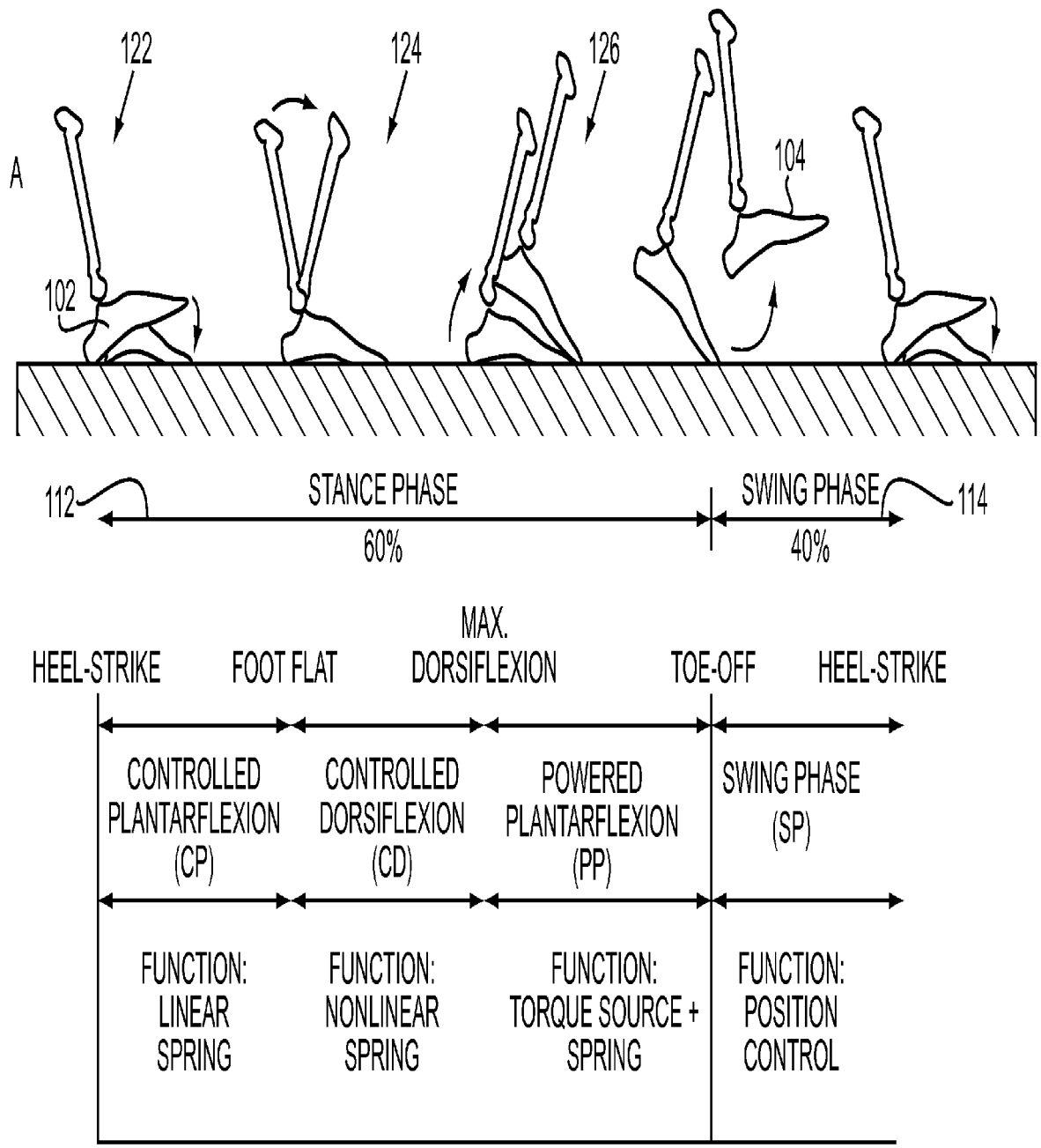
FIG. 1 depicts various phases of a human gait cycle.

The entire contents of each of U.S. patent application Ser. No. 12/157,727 "Powered Ankle-Foot Prosthesis" filed on Jun. 12, 2008 (Publication No. US2011/0257764 A1) and U.S. patent application Ser. No. 12/552,013 "Hybrid Terrain-Adaptive Lower-Extremity Systems" filed on Sep. 1, 2009 (Publication No. US2010/0179668 A1) are incorporated herein by reference. FIG. 1 illustrates normal ankle function in each of the four phases of a human gait cycle during level-ground ambulation. In the controlled plantar flexion state (CP) 122 during the stance phase 112, the ankle 102 serves as a linear spring impedance that cushions the foot-strike impact in accordance with the gait speed. In the controlled dorsiflexion state (CD) 124 during stance 112, the ankle 102 behaves as a non-linear spring that stores energy for later release in the powered plantar flexion state (PP) 126. In PP 126, the ankle 102 delivers a reflex response—an uncontrolled release of torque that both lifts and propels the wearer in accordance with gait speed. In the swing phase 114, the ankle 102 applies position control to first reposition the foot 104 after toe-off to achieve ground clearance and then to prepare the foot 104 for the foot strike initiation in the next gait cycle. The repositioning for toe-off and heel strike is generally accomplished through modulation of impedance and joint equilibrium so as to achieve, in the augmented system, the mass-spring-damper dynamics of the human ankle. In the swing phase, the repositioning and heel strike preparation is accomplished through modulation of the impedance and joint equilibrium to model human ankle spring-mass-damper dynamics for the augmented system.

Platform and PFO (described with reference to FIGS. 4a and 4b below) mimic human ankle behavior during the gait cycle—modulating impedance, torque and joint equilibrium in accordance with the gait cycle and speed and, optionally, terrain—and augments the ankle torque of the wearer, employing positive force feedback to mimic the calf muscle-Achilles tendon reflex response, thereby normalizing the ankle response as described below. A time-varying joint equilibrium (e.g., position and/or angle) in conjunction with an impedance (stiffness and damping) mimics the biomechanics. Therefore, a powered biomimetic orthosis (e.g., a PFO)—when worn by a wearer with posterior and/or anterior weakness—may deliver measurable benefits through reduction of leading leg impact force, reduction in metabolic cost-of-transport and increased walking speed.

With reference to FIG. 2a, if a wearer exhibits posterior weakness, the trailing leg 202 typically delivers reduced lifting force 212a at the time that the foot on the leading leg 204 strikes the ground. This deficiency in turn can increase the impact force 214a on the leading leg 204 and the "negative work" contribution during the weight transfer (transition) from the trailing to the leading leg. The body may attempt to adapt by applying additional "transition work" to counteract this negative work contribution, thereby increasing metabolism and reducing the self-selected walking speed. FIG. 2b illustrates that using biologically-inspired Platforms according to the invention, ankle torque is augmented during PP 126, thereby lifting the wearer's center-of-gravity at approximately the time of leading leg 204 impact, thereby reducing the impact force 214b and the negative work contribution. Consequent transition work reduction leads to reduced metabolic cost and an increased self-selected walking speed.

Figure 3:
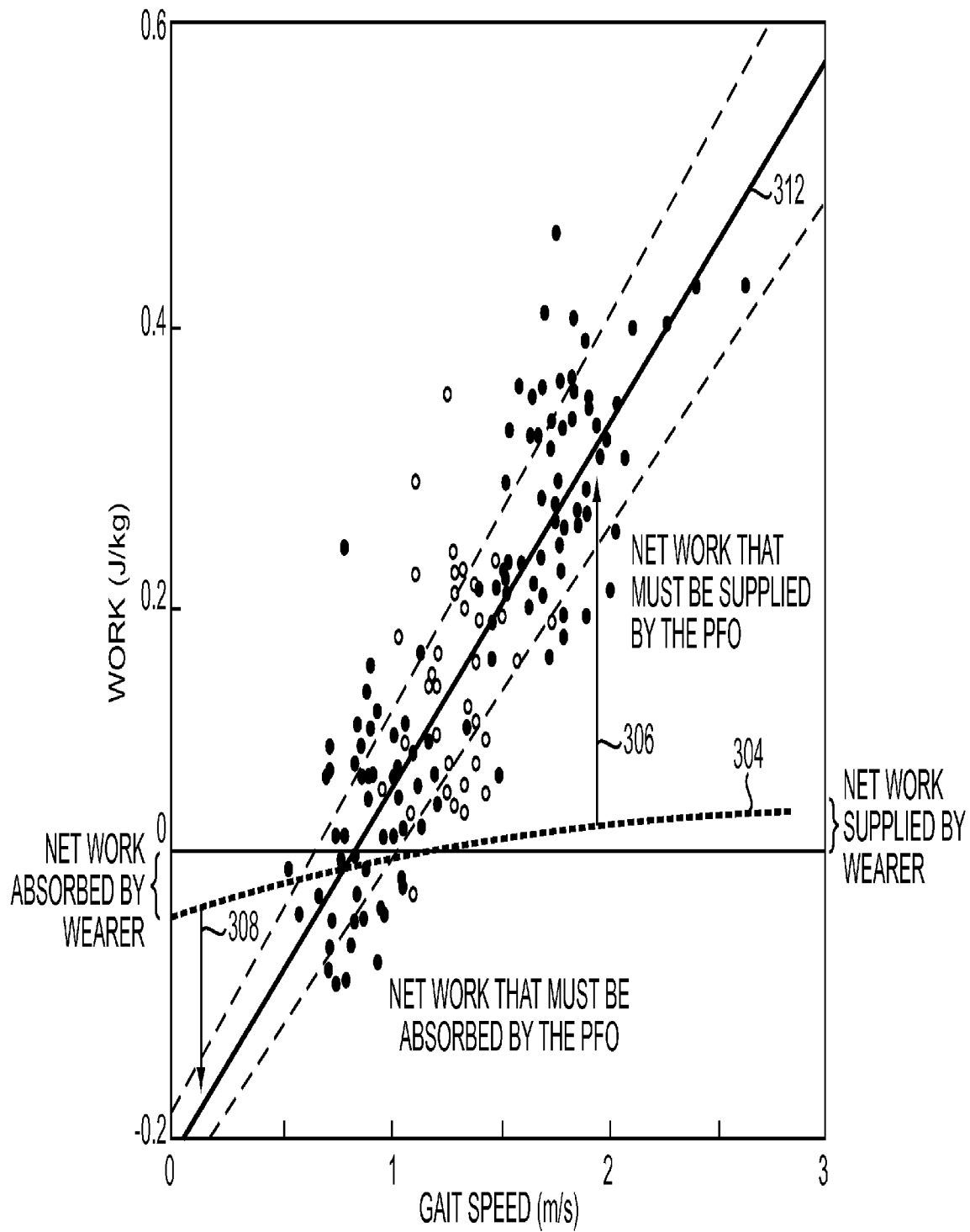
FIG. 3 shows the normalized work performed by a typical ankle during a gait cycle at different walking speeds.

FIG. 3 illustrates that in an intact ankle population, the normalized work performed by the ankle during a gait cycle varies generally linearly with gait speed, as shown by line 302. The dashed line 304 illustrates the deficiency implied by bilateral weakness. As shown by vectors 306, 308, the Platform must perform both positive and negative work to make up for the deficiencies and achieve a biomimetic response. Such work generally varies with gait speed.

Figure 5:
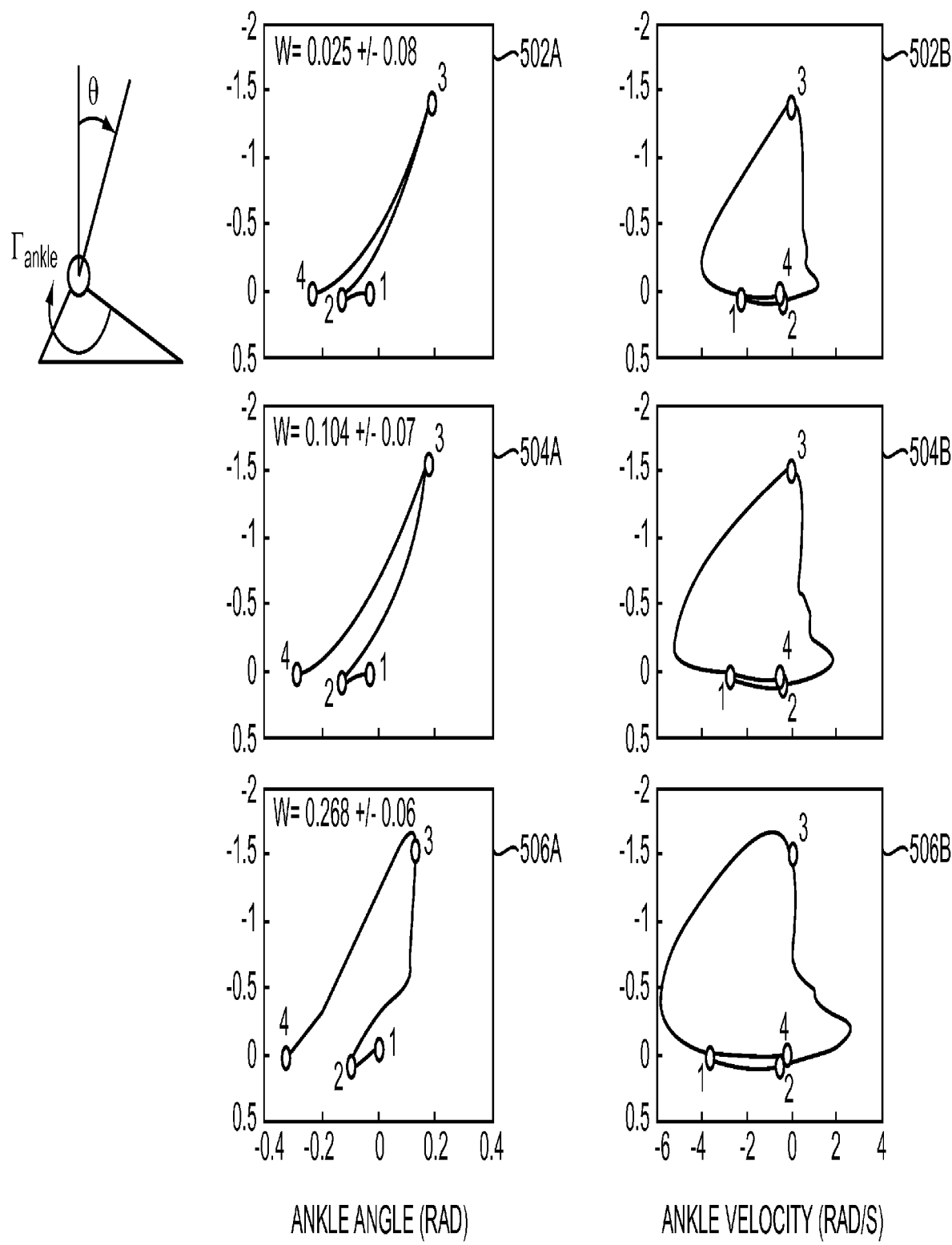
FIG. 5 depicts a relationship between ankle torque, ankle angle, and ankle-angle velocity for a typical ankle at different walking speeds.
Figure 6:
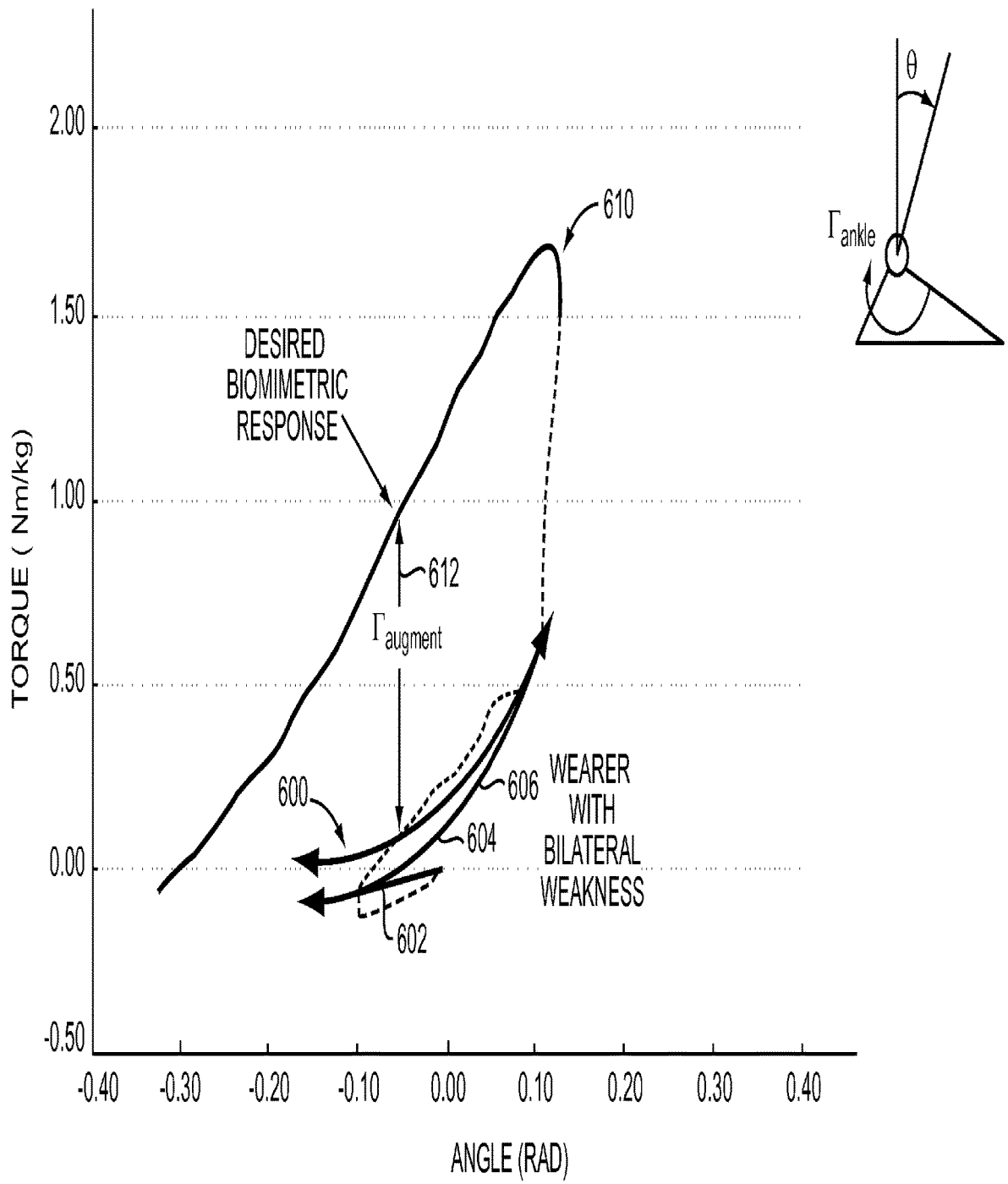
FIG. 6 depicts a augmentation of ankle torque according to one embodiment.

FIG. 4a schematically depicts the specifications and illustrates the actuator and control architecture employed to achieve them according to one embodiment of the invention. The Platform 400 is designed to be adapted to the full range of military and civilian personnel through use of a quiet, light-weight and rugged actuator 410. A modular battery 402 with a 2000 step capacity (wearer weighing 70 kg with bilateral deficiency) is employed. It is anticipated that a typical wearer will need to replace this lightweight battery pack between one and two times per day. The actuator 410 is designed so as to deliver at least a full biomimetic torque and angle response to cover a gait speed range from 0-1.75 m/sec. as discussed and shown in FIG. 5. Finally, the Platform 400 employs two embedded wireless interfaces 404. The Bluetooth interface serves as a pathway for PDA-based tuning by clinicians and researchers to normalize the torque response—specifically to program the Platform to deliver $\Gamma_{augment}$ (described below with reference to FIG. 8) as required in each phase of the gait cycle as shown in FIG. 6. The smart WiFi interface serves as a pathway for researchers to acquire control state variables and sensory feedback from the Platform 400 and to synchronize this telemetry with external biomechanical instrumentation.

As depicted in FIG. 4a, the Platform 400 employs a series-elastic actuator (SEA) 410 to drive the powered orthosis. See, for example, U.S. Pat. No. 5,650,704 "Elastic Actuator for Precise Force Control" the disclosure of which is incorporated herein by reference. As shown, a multi-processor control system (State and Actuator Controller) 422 uses feedback from the SEA 410 to deliver the appropriate response in accordance with the phase of the gait cycle and the walking speed and, optionally, according to the terrain and the wearer's activity thereon (e.g., walking upslope or downslope, ascending or descending stairs, etc.). A three-phase brushless motor driver (Motor Driver) 412 interfaces to the State and Actuator Controller 422 to accomplish closed-loop torque control of the SEA 410. An Inertial Measurement Unit (IMU) 424, employing a three-axis rate gyro and a three-axis accelerometer, provides feedback to sense state transitions within the gait cycle, to measure gait speed and to discriminate terrain modality. Terrain modality may refer to the type of the terrain such as level and/or sloping ground and stairs and, as such, discrimination of terrain modality may include determining a transition between different terrain types. A WiFi/Bluetooth communication module 404 is employed to interface directly to the State Controller and Actuator Controller 422 to facilitate research data acquisition and PDA-based clinician tuning.

The SEA 410 employs a robust ball-nut and ball-screw mechanism 414 driven by the high-rpm brushless motor 412 through a redundant aramid fiber twin belt transmission 416 to achieve about L1 design life of over five million cycles (i.e., a design whereby 99% of a population survive longer than the reported design life with 95% statistical confidence). The ball-nut 414 of the SEA 410 drives the foot support crank-arm mechanism through a bilateral spring assembly 418 exhibiting a weak stiffness in plantar flexion and a stiffer spring in dorsiflexion. In this application, the bilateral spring 418 is used 1) to store energy in controlled dorsiflexion for later release in the reflex response delivered in powered plantar flexion and 2) to serve as a sensing means for achieving closed-loop torque control of the actuator 410. By accomplishing the former, the peak power of the motor 412, and hence motor size and weight, may be reduced by over 40% compared to an actuator without the spring storage. In the latter, spring 418 displacement is used to estimate and thereby control drive torque in a way that attenuates the effect of friction—enabling a backdrivable means of actuation that mimics biology. Ankle angle sensor 432, motor position sensor 434, and ball-screw position sensor 436 embedded in the actuator 410 are employed to sense the state of the actuator 410 and to provide a basis for controlling the brushless motor 412 and for modulation of the PFO impedance, torque and position in accordance with the phase of the gait cycle and gait speed.

Figure 4B:
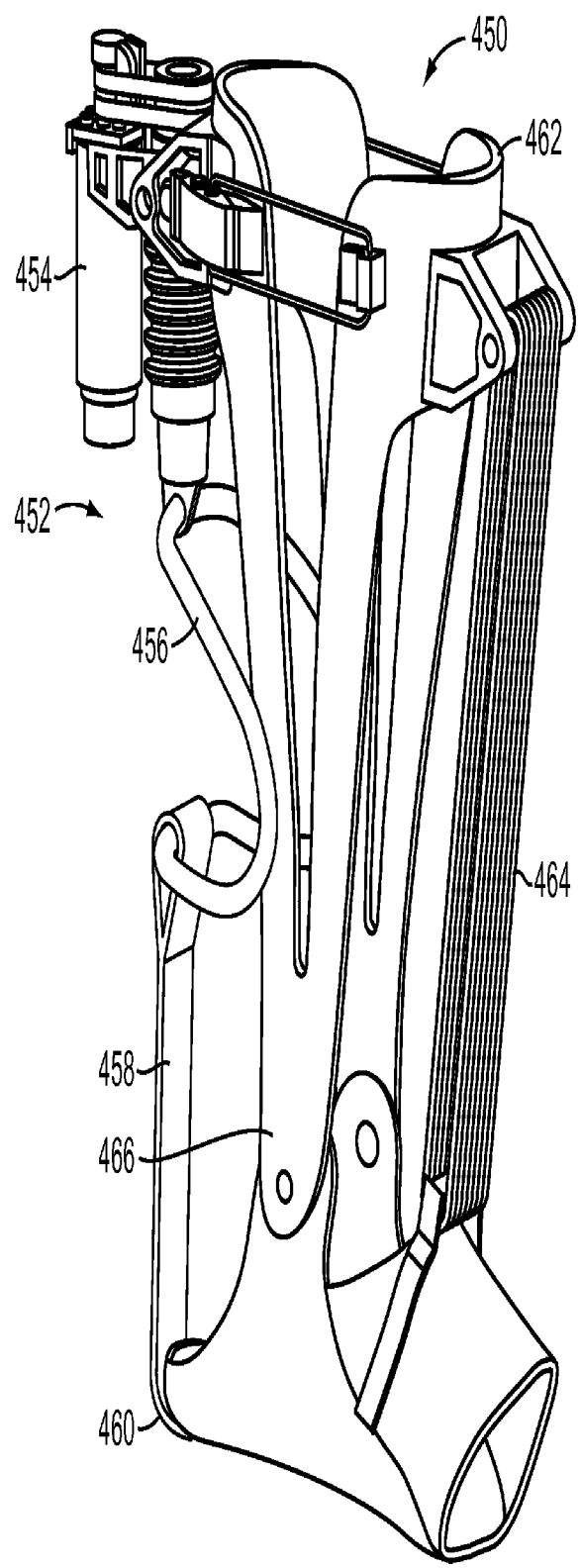

Another PFO device 450 shown in FIG. 4b includes a SEA 452 which includes a motor 454, redundant belt drive and ball nut/screw transmission and an elastic element 456 in series. The motor 454 can be a transverse-flux or other efficient, high-torque motor, optionally eliminating the belt drive for a direct drive system. The elastic element 456 is in communication with a stiff element 458, which is coupled to an elastomer foot support 460. A cuff 462 that may be adapted for a comfortable fit to a lower-leg portion of a wearer is coupled to the SEA 452. A controller circuitry for controlling the SEA 452 may be mounted on a housing of the SEA 452 and an inertial measurement unit may be mounted on the cuff 462. A parallel elastic element 464 is coupled to the cuff 462 and the elastomer 460 anterior of the ankle pivot joint 466, in opposition to the SEA 452 and element 458 disposed posterior of the joint 466.

A biomimetic response can be described in terms of various parameters such as joint torque, joint power, joint angle, etc., and other related parameters such as net work. These parameters generally vary with walking speed. Therefore, relationships between joint power and walking speed, net work and walking speed, etc., individually or in combination, generally provide a projection of a biomimetic response. In FIG. 5, chart 502a depicts representative ankle torque and ankle angle, and chart 502b depicts representative ankle torque and ankle-angle velocity of a typical ankle at a walking speed of about 0.75 m/sec. Similarly, charts 504a, 504b depict representative ankle torque and ankle angle, and ankle torque and ankle-angle velocity, respectively, of a typical ankle at a walking speed of about 1.25 m/sec. Charts 506a, 506b depict representative ankle torque and ankle angle, and ankle torque and ankle-angle velocity, respectively, of a typical ankle at a walking speed of about 1.75 m/sec. In each of these charts, a transition from data-point 1 to data-point 2 corresponds to the CP state, a transition from data-point 2 to data-point 3 corresponds to the CD state, a transition from data-point 3 to data-point 4 corresponds to the PP state, and a transition from data-point 4 back to data-point 1 corresponds to the swing phase.

With reference to FIG. 6, the portion 602 of the ankle-torque with respect to ankle-angle curve 600 corresponds to the CP phase of a wearer whose joint (e.g., ankle, knee, etc.) function is diminished so as to exhibit bilateral weakness. The portion 604 corresponds to the CD phase of the curve 600, and the portion 606 corresponds to the PP phase of the curve 600. A desired biomimetic response is depicted by the curve 610. In order to achieve such a response, an augmentation torque, $\Gamma_{augment}$ 612 may be supplied to the joint (e.g., ankle, knee, etc.). The Platform 400 and/or the PFO 450 described above can be controlled as described below with reference to FIGS. 7 and 8, so as to provide the augmentation torque $\Gamma_{augment}$ 612 such that a desired biomimetic response 610 according to the wearer's walking speed (e.g., as shown in FIG. 5) can be achieved.

Figure 7:
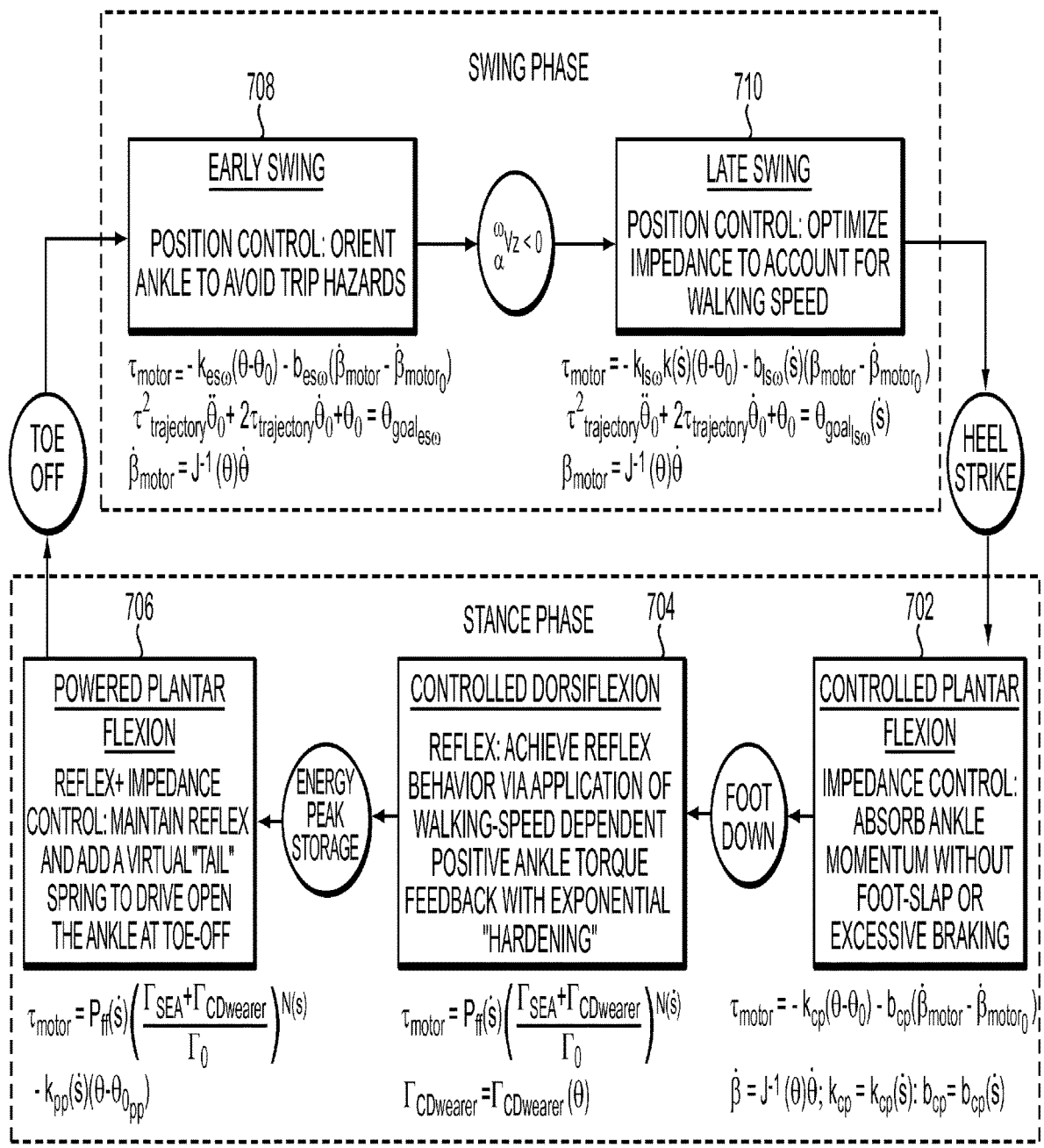
FIG. 7 schematically illustrates various states of a controller for controlling a PFO device according to one embodiment.

With reference to FIG. 7, the biologically-inspired state machine 700 that substantially implements various joint functionalities described with reference to FIG. 1 includes a Controlled Plantar Flexion State 702. The Platform 400 or PFO 450 applies a linear spring and damping impedance in accordance with the walking speed based on:

$$T_{motor} = -k_{cp}(\theta - \theta_0) - b_{cp}(\dot{\beta}_{motor} - \dot{\beta}_{motor_0})$$

$$\dot{\beta} = J^{-1}(\theta)\dot{\theta}; \ k_{cp} = k_{cp}(\dot{s}); \ b_{cp} = b_{cp}(\dot{s})$$

where $T_{motor}$ is the commanded SEA motor torque;

$\theta$ is the ankle angle;

$\beta_{motor}$ is the motor angle corresponding to the ankle angle;

$\dot{s}$ is the estimated gait speed at foot-strike estimated by the IMU; and

J is the Jacobian that relates motor speed, $d\beta/dt$ to $d\theta/dt$ as above assuming no spring deflection. The Jacobian captures the non-linear relationship arising from the actuator-joint linkage kinematics.

The mass of the motor 454 can provide an inertial component in addition to the linear spring and/or damping components.

Transition into this state 702 is accomplished by sensing by the IMU 424 the distinctive vibration that typically occurs when the foot strikes the ground. The impedance of the joint may be configured and scaled so as to prevent foot slap in accordance with walking speed and the response needed to normalize the augmented response of the wearer.

Transition into the Controlled Dorsiflexion State 704 is accomplished when the ankle angle velocity detected by the IMU 424 and/or the ankle sensor 432 switches positive, typically when the foot-flat condition is achieved. In this state 704, a reflex response is achieved through non-linear positive feedback, as defined in the relation:

$$\tau_{motor} = P_{ff}(\dot{s})\left(\frac{\Gamma_{SEA} + \Gamma_{CDwearer}}{\Gamma_0}\right)^{N(\dot{s})}$$

$$\Gamma_{CD_{wearer}} = \Gamma_{CD_{wearer}}(\theta)$$

In this, the reflex/positive-feedback gain $P_{ff}(\dot{s})$ and the exponent (non-linear spring) $N(\dot{s})$ are both functions of the estimated gait speed at foot-flat. $\Gamma_0$ is a normalizing torque comparable to the maximum torque in dorsiflexion at the self-selected walking speed. $\Gamma_{SEA}$ is the torque in the series spring. A "hard stop" spring model, $\Gamma_{CD_{wearer}}(\theta)$, is used to model the wearer torque response at extremes of dorsiflexion ($\theta > 0$) so that at least a biomimetic response can be achieved. In the equations above, functions of velocity can, by those proficient in the art, be extended to include terrain activity, including slope and stair. Generally, ascent of slope and stair will require higher positive force feedback gain and lower exponent. Descent of slope and stair will generally require lower gain and higher exponent. Ascent of slopes will generally require lower CP stiffness while descent of slopes will generally require higher damping.

Transition into the Powered Plantar Flexion State 706 is accomplished when the ankle angle velocity switches negative. The reflex response is augmented by a "tail spring" (e.g., elastic element 456) to drive full plantar flexion of the ankle per the relation:

$$\tau_{motor} = P_{ff}(\dot{s})\left(\frac{\Gamma_{SEA} + \Gamma_{CDwearer}}{\Gamma_0}\right)^{N(\dot{s})} - k_{pp}(\dot{s})(\theta - \theta_{0_{pp}})$$

where $\theta_{0_{pp}}$ is the desired equilibrium state of the ankle in plantar flexion.

$P_{ff}(\dot{s})$, $N(\dot{s})$, $k_{pp}$, and $k_{cd}$ can be functions of terrain modality, as described above to reduce the net non-conservative work when going downslope, descending stairs, etc. and to increase the net non-conservative work when going upslope, ascending stairs, etc.

Transition into Early Swing State 708 occurs when the detected SEA 410 torque, $\Gamma_{SEA}$, approaches a programmable percentage of peak torque, generally a small percentage of the peak torque indicating that the toe is off or nearly off the ground. In this state 708, position control (impedance control with an over-damped joint equilibrium trajectory) is employed to achieve proper ground clearance through use of an organically-derived trajectory, $\theta_0(t)$ that smoothly transitions to a goal position, $\theta_{goal}=0$ to simulate an overdamped inertia-spring-damper mechanical response.

Transition into Late Swing State 710 occurs when the IMU 424 detects a negative, vertical Cartesian (world-frame referenced) velocity, $^wV_z$. In this state, position control is again used but with a smooth trajectory that converges to a time-varying goal point, $\theta_{goal}$, that is a function of gait speed and terrain slope, each estimated by the IMU 424. The impedance (stiffness and damping) applied to position and velocity errors referenced to the trajectory (equilibrium) $\theta_0(t)$ is set in accordance with gait speed and terrain angle. In the case of stair descent, the equilibrium angle may be set to a plantar flexed position and impedance can be heavily damped impedance to absorb energy in toe-strike.

Figure 8:
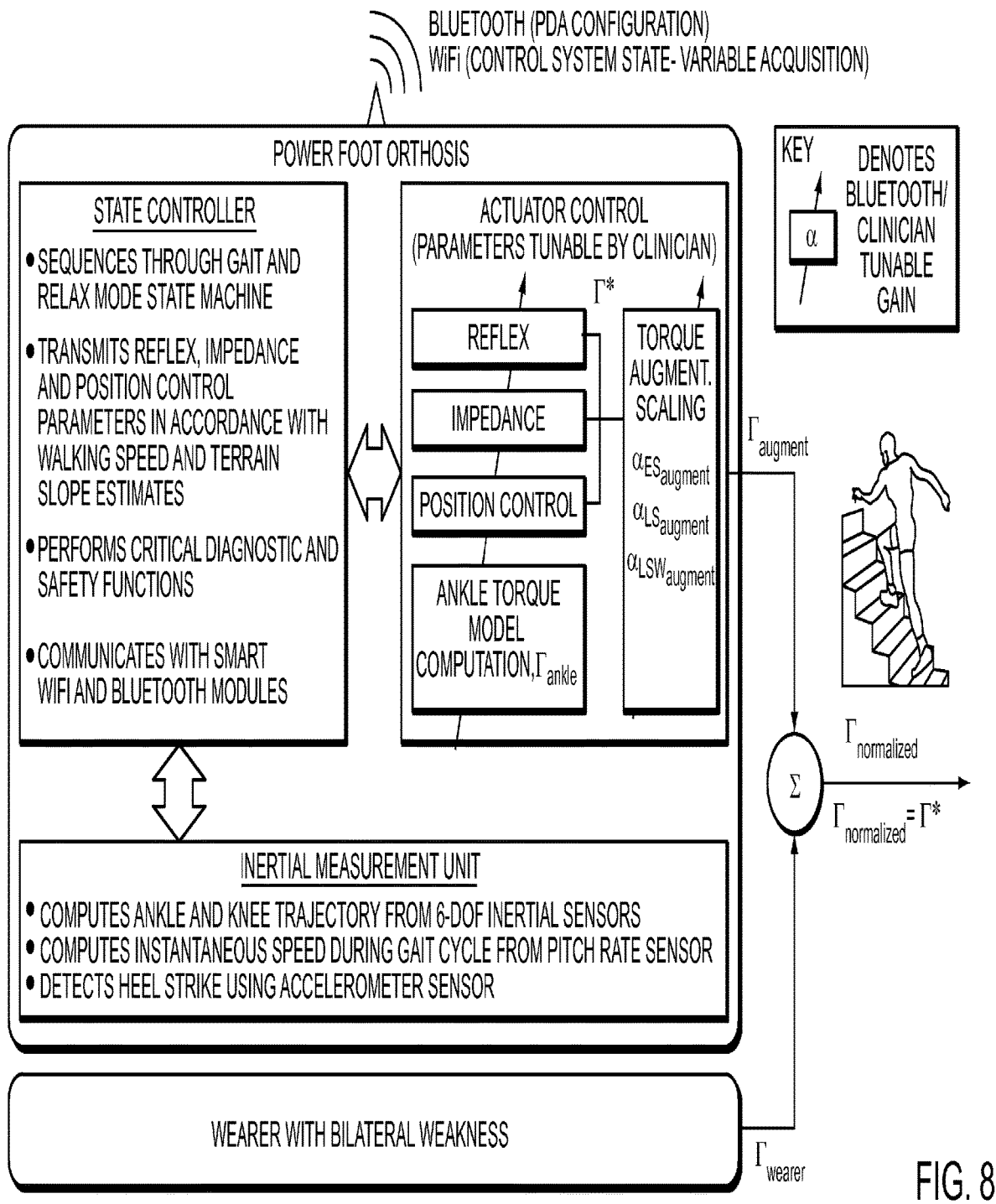
FIG. 8 schematically illustrates operation of the controller of FIG. 7 according to one embodiment.

FIG. 8 illustrates how the Platform 400 or PFO 450 can augment the torque of the wearer to achieve a normalized biomimetic response. In other embodiments, the Platform 400 or PFO 450 can augment the torque of the wearer to achieve a response that can enable a wearer who does not have a diminished natural joint function to perform activities such as walking or running a long distance, carrying a heavy load, etc. The state machine 700 modulates the SEA 410 impedance, reflex and position control response in accordance with gait speed and terrain modality inputs from the IMU 424. The SEA control internally computes the normalized biomimetic torque, $\Gamma^*$, in each state of the gait cycle. State-specific attenuation, set initially by the clinician, then scales $\Gamma^*$ and drives the SEA 410 to deliver just the right torque, $\Gamma_{augment}$, to add to the wearer torque response, $\Gamma_{wearer}$, to approximate $\Gamma^*$, the desired normalized biomimetic response.

Figure 9:
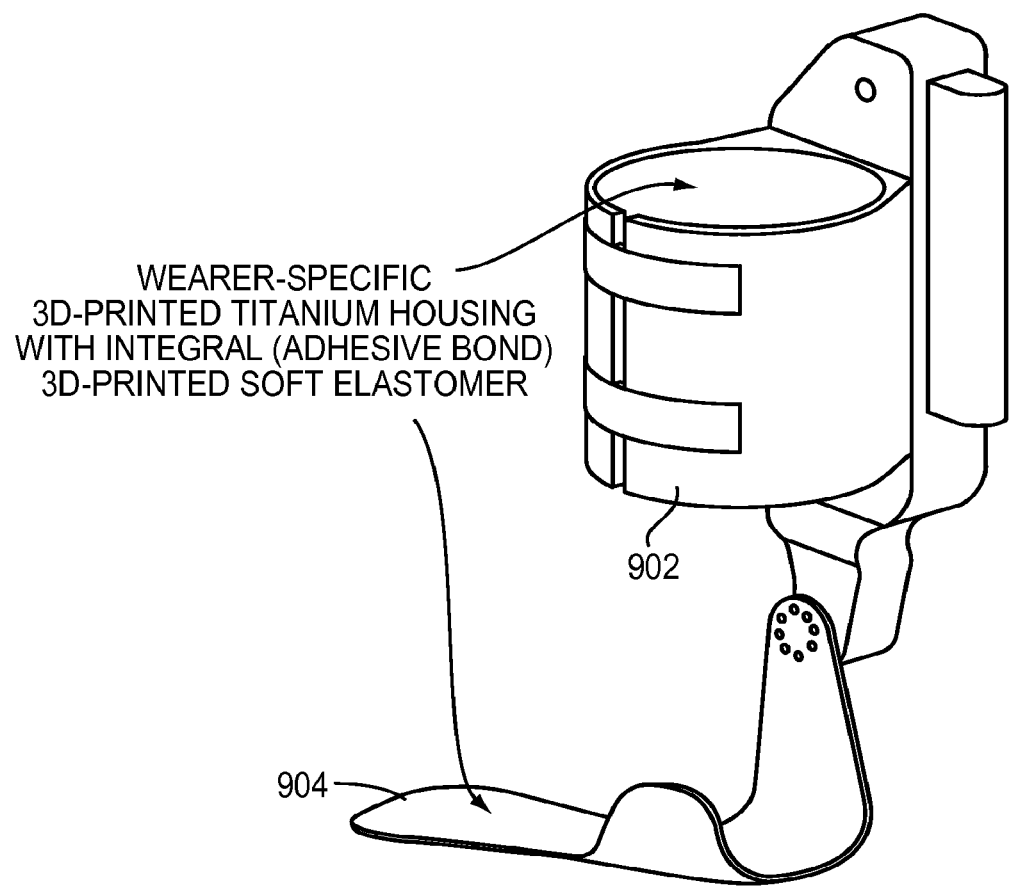
FIG. 9 illustrates seamless integration of a PFO with a lower leg of a human according to one embodiment.

Seamless integration of the Platform 400 or PFO 450 onto a wearer can be important to ensure that the PFO-supplied torque is coupled efficiently. To achieve widespread utility of the wearable robotic technology described herein, a process is developed for custom manufacturing a cuff and foot assembly 902 shown in FIG. 9 that may conform/couple directly to the lower extremity of the wearer. For each wearer 3-D scanning tools measure those body surfaces that integrate with the Platform 400 or PFO 450. From these surface measurements, a direct-write process can print lightweight titanium or carbon-fiber forms that can be functionalized through heat treatment to create the scaffold upon which a custom 3-D printed elastomer 904, with spatially-varying durometer, can be bonded to achieve the desired custom integration.

In some embodiments, the State and Actuator Controller 422 is adapted to kinematically reconstruct a joint path. Such reconstruction can be used to determine the terrain (e.g., whether the terrain is level ground, sloping ground, or stairs), and activity (i.e., whether the wearer is walking on level ground, upslope, or downslope, or walking up or down the stairs). The modulation of the toque, impedance, and joint equilibrium may be based on the terrain and activity as determined via the kinematic reconstruction.

Figure 10:
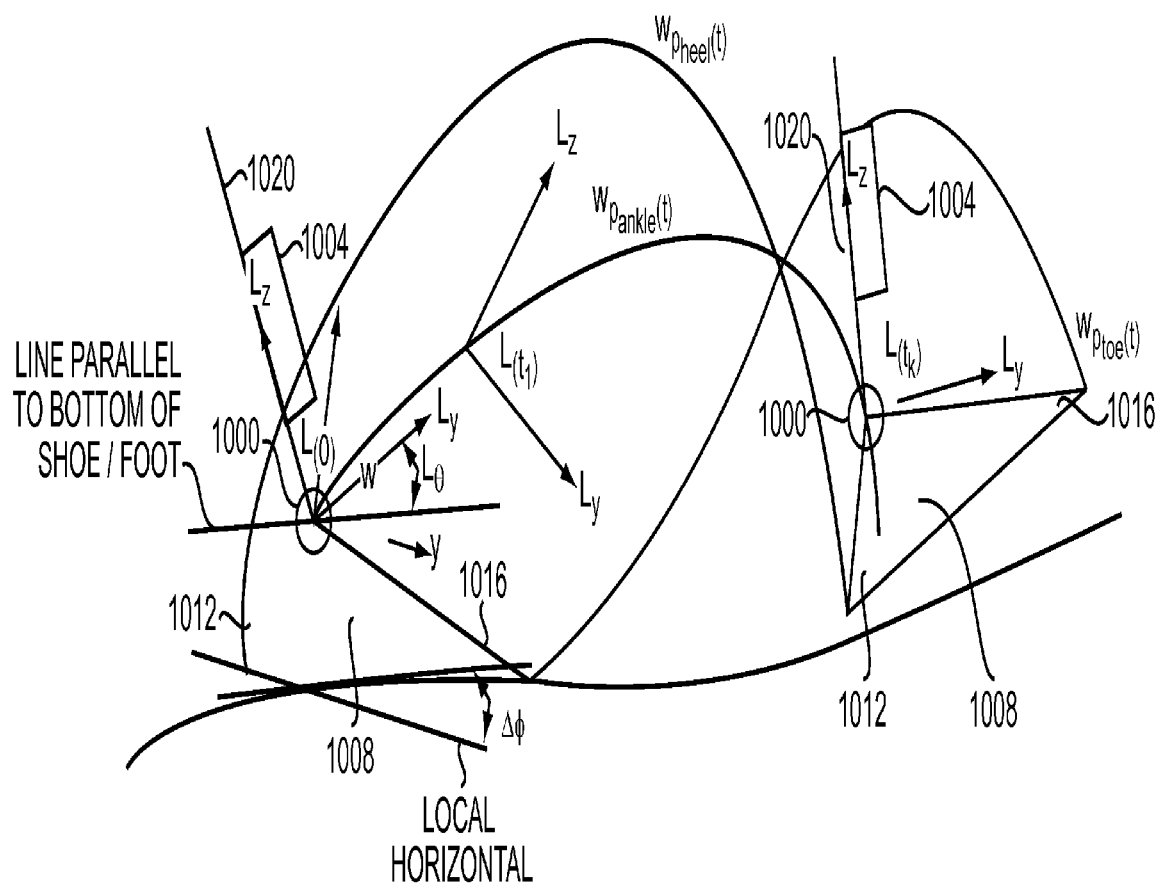
FIG. 10 depicts kinematic reconstruction by a controller for controlling a PFO according to one embodiment.

FIG. 10 illustrates a method for determining, via kinematic reconstruction, ankle joint 1000, heel 1012 and toe 1016 paths while using any PFO (e.g., the Platform 400 or the PFO 450) based on the inertial pose of a lower leg member 1020 coupled to the ankle joint 1000, and the angle between the lower leg member 1020 and foot member 1008. Pose is the position and orientation of a coordinate system. The IMU 424 may be coupled to the lower leg member 1020. The IMU 424 may include a three-axis rate gyro for measuring angular rate and a three-axis accelerometer for measuring acceleration. Placing the inertial measurement unit on the lower leg member 1020 collocates the measurement of angular rate and acceleration for all three axes of the lower leg member 1020. The inertial measurement unit 424 provides a six-degree-of-freedom estimate of the lower leg member 1020 pose, inertial (world frame referenced) orientation and ankle-joint 1000 (center of rotation of the ankle-foot) location.

In some embodiments, the lower leg member 1020 pose is used to compute the instantaneous location of the knee joint. By using knowledge of the ankle joint 1000 angle ($\theta$) the instantaneous pose of the bottom of the foot 1008 can be computed, including location of the heel 1012 and toe 1016. This information in turn can be used when the foot member 1008 is flat to measure the terrain angle in the plane defined by the rotational axis of the ankle joint/foot member. Mounting the inertial measurement unit 424 on the lower leg member 1020 has advantages over other potential locations.

Unlike if it were mounted on the foot member 1008, the lower leg member 1020 mounting protects against physical abuse and keeps it away from water exposure. Further, it eliminates the cable tether that would otherwise be needed if it were on the foot member 1008—thereby ensuring mechanical and electrical integrity. Finally, the lower leg member 1020 is centrally located within the kinematic chain of a hybrid system facilitating the computation of the thigh and torso pose with a minimum of additional sensors.

The inertial measurement unit 424 can be used to calculate the orientation, $$^w_{ankle}O,$$

position, $$^w_{ankle}p,$$

and velocity, $$^w_{ankle}v,$$

of the PFO (e.g., Platform 400, the PFO 450, etc.) in a ground-referenced world frame.

$$^w_{ankle}O$$

may be represented by a quaternion or by a 3×3 matrix of unit vectors that define the orientation of the x, y and z axes of the ankle joint in relation to the world frame. The ankle joint 1000 coordinate frame is defined to be positioned at the center of the ankle joint axis of rotation with its orientation tied to the lower leg member 1020. From this central point, the position, velocity and acceleration can be computed. For points of interest in, for example, the foot (e.g., the heel 1012 or toe 1016), a foot member-to-ankle joint orientation transformation, $$^{ankle}_{foot}O(\theta)$$

is used to derive the position using the following relation:

$$^w_{point-of-interest}p = {}^w_{ankle}p + {}^w_{ankle}O(\gamma)^{ankle}_{foot}O(\theta)(^{foot}r_{point-of-interest})$$

where $$^{ankle}_{foot}O(\gamma) = \begin{bmatrix} 1 & 0 & 0 \\ 0 & \cos(\gamma) & -\sin(\gamma) \\ 0 & \sin(\gamma) & \cos(\gamma) \end{bmatrix}$$

where γ is the inertial lower leg member angle, and $$^{ankle}_{foot}O(\theta) = \begin{bmatrix} 1 & 0 & 0 \\ 0 & \cos(\gamma) & -\sin(\gamma) \\ 0 & \sin(\gamma) & \cos(\gamma) \end{bmatrix}$$

where θ is the ankle joint angle.

In this embodiment, the inertial measurement unit 424, including the three-axis accelerometer and three-axis rate gyro, is located on the forward face at the top of the lower leg member 1020. It is advantageous to remove the effect of scale, drift and cross-coupling on the world-frame orientation, velocity and position estimates introduced by numerical integrations of the accelerometer and rate gyro signals Inertial navigation systems typically employ a zero-velocity update (ZVUP) periodically by averaging over an extended period of time, usually seconds to minutes. This placement of the inertial measurement unit is almost never stationary in the lower-extremity devices such as a PFO. However, the bottom of the foot is the only stationary location, and then only during the controlled dorsiflexion state of the gait cycle. An exemplary zero-velocity update method, which is not impacted by this limitation, for use with various embodiments of the invention is described further below.

To solve this problem, orientation, velocity and position integration of ankle joint is performed. After digitizing the inertial measurement unit acceleration, $IMU_\alpha$, the ankle joint acceleration ($IMU_{\alpha_{ankle}}$) is derived with the following rigid body dynamic equation:

$$^{IMU}a_{ankle} = {}^{IMU}a + {}^{IMU}\vec{\omega} X {}^{IMU}\vec{\omega} X^{IMU}_{ankle}\vec{r} + \vec{\dot{\omega}} X^{IMU}_{ankle}\vec{r}$$

where $IMU\vec{\omega}$ and $$IMU\vec{\dot{\omega}}$$

are the vectors of angular rate and angular acceleration, respectively, in the inertial measurement unit frame and X denotes the cross-product.

The relationship is solved $$^w_{ankle}O = {}^w_{IMU}O$$

similarly as in the equations above using standard strapdown inertial measurement unit integration methods, in accordance with the following relationships known to one skilled in the art:

$$_{ankle}^w\hat{\Phi} = {}^w\hat{\Omega}(^w\hat{\omega})_{ankle}^w\hat{\Phi}$$

$$^w\hat{V}_{ankle} = {}^w\hat{a}_{ankle} - [0, 0, g]^T$$

$$^w\hat{P}_{ankle} = {}^w\hat{V}_{ankle}$$

$$_{foot}^w\hat{\Phi} = {}_{ankle}^w\hat{\Phi}_{foot}^{ankle}\hat{\Phi} = {}_{ankle}^w\hat{\Phi} \text{ Rotation}_x(\hat{\theta})$$

$$^w\hat{V}_{heel} = {}^w\hat{V}_{ankle} + {}^w\hat{\Omega}\left(_{ankle}^w\hat{\Phi}[\hat{\theta}\ 0\ 0]^T\right)^w r_{heel-ankle}$$

$$^w\hat{V}_{toe} = {}^w\hat{V}_{ankle} + {}^w\hat{\Omega}\left(_{ankle}^w\hat{\Phi}[\hat{\theta}\ 0\ 0]^T\right)^w r_{toe-ankle}$$

$$^w\hat{P}_{heel} = {}^w\hat{P}_{ankle} + {}^w r_{heel-ankle}$$

$$^w\hat{P}_{toe} = {}^w\hat{P}_{ankle} + {}^w r_{toe-ankle}$$

$$^w r_{heel-ankle} = {}_{ankle}^w\hat{\Phi}^{foot}(r_{heel} - r_{ankle})$$

$$^w r_{toe-ankle} = {}_{foot}^w\hat{\Phi}^{foot}(r_{toe} - r_{ankle})$$

In the equations above, the matrix, $\hat{\Phi}$, will be used interchangeably with the orientation matrix, $$^w_{IMU}O.$$

The world frame-referenced ankle joint velocity and position are then derived at a point in time after the time of the previous zero-velocity update (i-th zero-velocity update) based on the following:

$$^wv_{ankle}(t) = \int_{ZVUP(i)}^{t} (^w_{IMU}O)^{IMU}a_{ankle}dt$$

$$^wp_{ankle}(t=ZVUP(i))^wp_{ankle}(t) = \int_{ZVUP(i)}^{t} {}^wv_{ankle}dt$$

where $^wp_{ankle}(t=ZVUP(i))$ is reset to zero for all i.

Figure 11A:
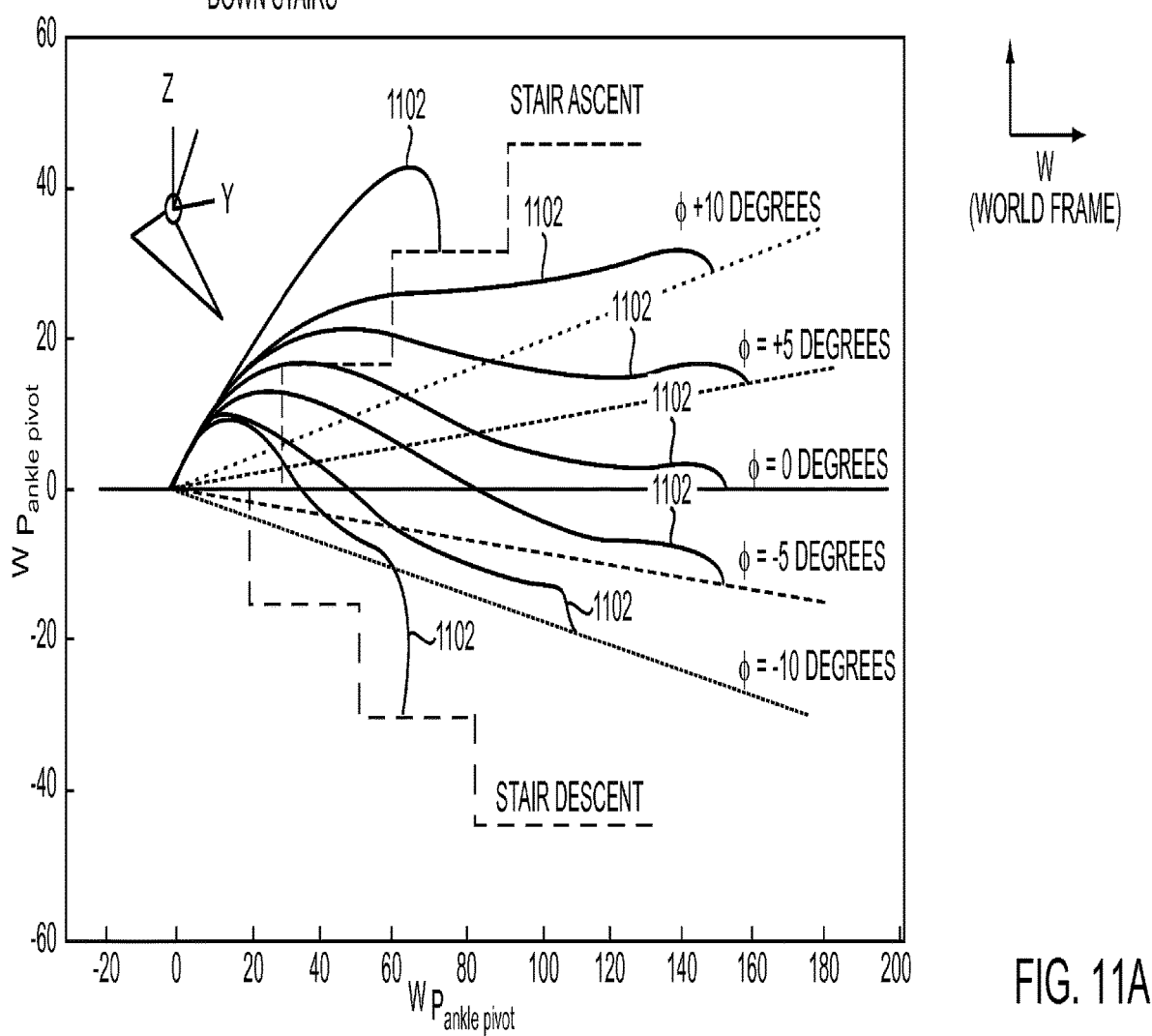
FIGS. 11a and 11b depict ankle and knee paths, respectively, each derived using measurements from an inertial measurement unit, according to one embodiment.

The six-degree-of-freedom inertial measurement unit (IMU) 424 of the Platform 400 or the PFO 450 is capable of computing the path of the ankle joint and the distal-end of the femur (knee) from which the IMU 424 can discriminate and discern terrain modality—including stairs and slopes. With reference to FIG. 11a, inertially referenced ankle joint paths 1102, $^wp_{ankle\ joint}(t)$, and ankle-velocity-attack-angle 1104, $w^V_{ankle\ joint}$, on stairs and sloping ground can be used to discriminate stair ascent/descent from ascent/descent on sloping ground. The slope, $\phi$, can be estimated as $\hat{\phi}$ in swing using the relation:

$$\hat{\phi} = \tan^{-1}(^wp_{ankle\ joint_z}(t), {}^wp_{ankle\ joint_y})$$

Figure 11B:
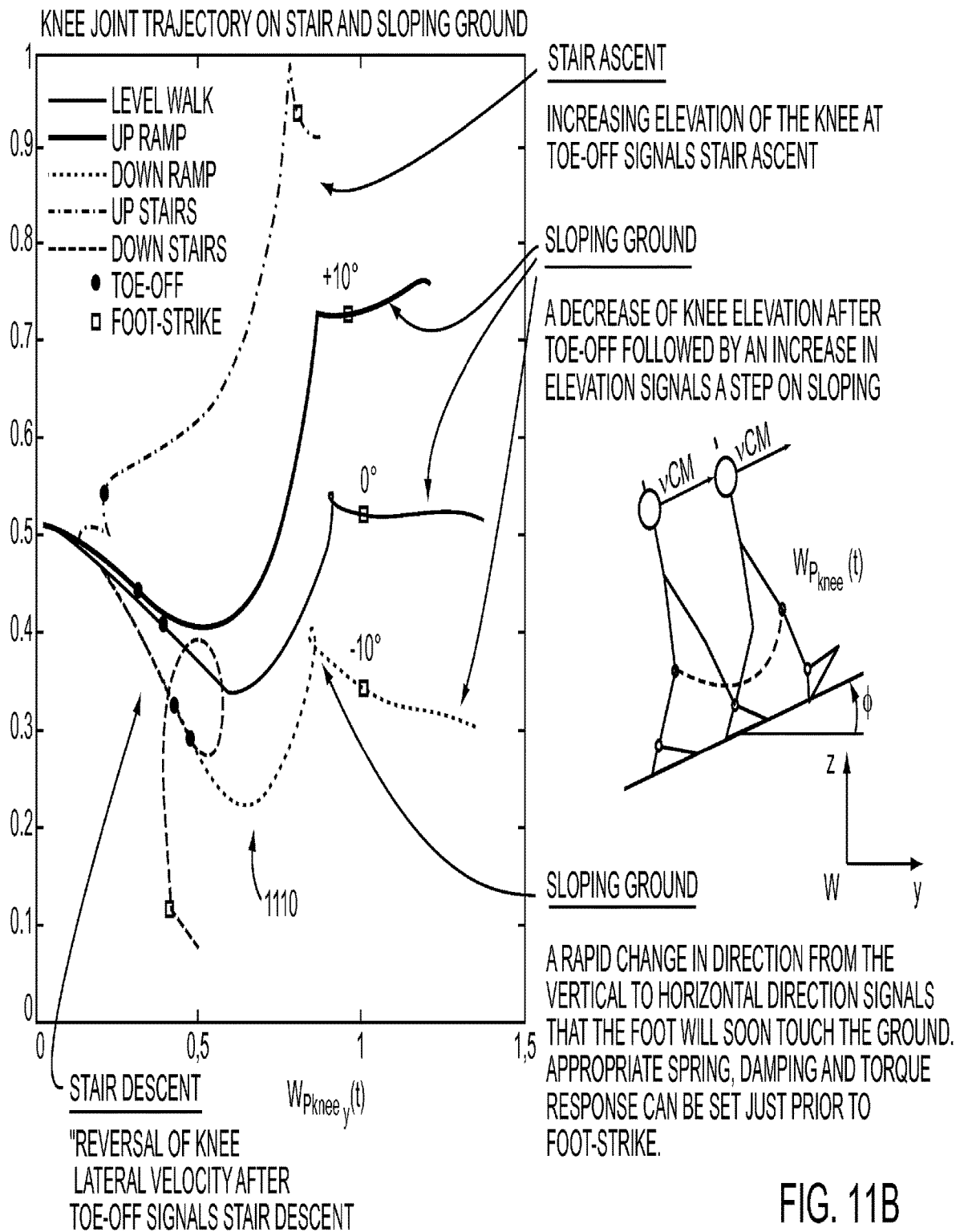

With reference to FIG. 11b, inertially-referenced knee path shape can be used to detect stair ascent/descent shortly after toe-off—enabling knee impedance and torque response to be configured prior to foot-strike on the stair. The "kink" 1110 in the knee path may signal impending foot strike on sloping ground, enabling a prediction of terrain slope using the ankle joint slope prediction described above with reference to FIG. 11a. Using the joint slope, speed and ankle velocity angle-of-attack, the joint equilibrium and impedance can be adjusted in preparation for the foot strike.

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A method for augmenting a joint function of a human during a gait cycle, the method comprising:
    providing a powered actuator configured to supply at least one of an augmentation torque and an impedance to a joint and a controller configured to modulate the augmentation torque and the impedance;
    compute, using the controller, a normalized biomimetic torque for a phase of the gait cycle, the normalized biomimetic torque according to a speed of ambulation, a terrain, or both a speed of ambulation and a terrain;
    retrieve, using the controller, a state-specific attenuation factor for the phase of the gait cycle;
    scale, using the controller, the normalized biomimetic torque based on the state-specific attenuation factor to determine the augmentation torque; and
    apply, using the powered actuator, the augmentation torque to the joint to provide at least a biomimetic response.

2. The method of claim 1, wherein the impedance comprises at least one of a stiffness component, a damping component, and an inertial component, and further comprising modulating the impedance by determining at least one of the stiffness component and the damping component.

3. The method of claim 1, wherein the impedance comprises a non-linear impedance, and further comprising modulating the impedance by determining a gain of the non-linear impedance and an exponent of the non-linear impedance.

4. The method of claim 1, wherein the augmentation torque is modulated according to the phase of the gait cycle that is determined, at least in part, according to at least one of a direction of joint angular velocity, joint angular velocity, joint inertial rate, joint acceleration, or a joint torque applied to the joint.

5. The method of claim 1, wherein the augmentation torque is supplied in addition to natural joint torque supplied by the human to achieve a pre-determined total joint torque response.

6. The method of claim 1, wherein applying the augmentation torque comprises applying a closed-loop torque control at the joint.

7. The method of claim 4, further comprising: modeling the joint torque applied to the joint; and determining the phase of the gait cycle based on a joint torque model.

8. The method of claim 1, further comprising generating a kinematic reconstruction by kinematically reconstructing a path of a proximal link connected to at least one of the joint and another joint proximal to the joint, within the gait cycle.

9. The method of claim 8, wherein the kinematic reconstruction comprises determining a terrain type as one of substantially level surface, sloping surface, and stairs.

10. The method of claim 9, wherein the kinematic reconstruction comprises determining an activity according to the terrain type, the activity being one of ascending stairs, descending stairs, walking on substantially level surface, walking on a surface sloping up, and walking on a surface sloping down.

11. The method of claim 1, wherein the impedance is supplied to the joint during a controlled plantar flexion phase of the gait cycle in order to mitigate foot slap.

12. The method of claim 1, wherein the augmentation torque, the impedance, and a joint equilibrium are modulated in order to mitigate foot drop.

13. The method of claim 1, wherein the augmentation torque, the impedance, and a joint equilibrium are modulated in order to provide a pre-determined net work according to at least one of the speed of ambulation and the terrain.

14. The method of claim 1, wherein the augmentation torque is modulated according to a positive-force feedback.

15. The method of claim 14, wherein the augmentation torque is modulated according to the positive-force feedback in combination with a natural joint torque supplied by the human to approximate a normal joint torque.

16. The method of claim 14, wherein the positive-force feedback comprises a gain and an exponent.

17. The method of claim 16, wherein at least one of the gain and the exponent is determined according to at least one of the speed of ambulation and the terrain.

* * * * *